United States Patent
Jain et al.

(10) Patent No.: US 9,936,876 B2
(45) Date of Patent: Apr. 10, 2018

(54) ROBUST POWERING OF IMPLANTABLE BIOSENSOR PLATFORM

(75) Inventors: Faquir Chand Jain, Storrs, CT (US); Fotios Papadimitrakopoulos, West Hartford, CT (US)

(73) Assignee: OPTOELECTRONICS SYSTEMS CONSULTING, INC, Storrs, CT (US)

(*) Notice: Subject to any disclaimer, the term of this patent is extended or adjusted under 35 U.S.C. 154(b) by 98 days.

(21) Appl. No.: 13/421,513

(22) Filed: Mar. 15, 2012

(65) Prior Publication Data
US 2012/0323092 A1 Dec. 20, 2012

Related U.S. Application Data

(60) Provisional application No. 61/452,912, filed on Mar. 15, 2011.

(51) Int. Cl.
| | |
|---|---|
| *A61B 5/1455* | (2006.01) |
| *A61B 5/00* | (2006.01) |
| *A61B 5/1459* | (2006.01) |
| *A61B 5/145* | (2006.01) |

(52) U.S. Cl.
CPC .......... *A61B 5/0017* (2013.01); *A61B 5/1459* (2013.01); *A61B 5/14532* (2013.01); *A61B 2560/0219* (2013.01)

(58) Field of Classification Search
CPC .................................... A61B 5/1455
USPC .................................. 600/310–344
See application file for complete search history.

(56) References Cited

U.S. PATENT DOCUMENTS

| | | | | |
|---|---|---|---|---|
| 5,627,380 A | * | 5/1997 | Crowne | 250/577 |
| 5,637,155 A | * | 6/1997 | Inoue | 136/244 |
| 2008/0154101 A1 | * | 6/2008 | Jain et al. | 600/309 |

* cited by examiner

*Primary Examiner* — Eric Winakur
*Assistant Examiner* — Marjan Fardanesh
(74) *Attorney, Agent, or Firm* — Steven M. McHugh

(57) ABSTRACT

An implantable device for measuring biological information of a body is provided, wherein the implantable device includes a receiver for receiving electromagnetic energy and converting the electromagnetic energy into electrical energy; a storage capacitor associated with the receiver such that the electrical energy from the receiver is stored in the storage capacitor; a biological sensor; a processing device; and a transmitter, wherein the biological sensor, processing device and transmitter are configured to receive electrical energy from the storage capacitor, and wherein the biological sensor, processing device and transmitter are configured such that when the receiver is receiving electromagnetic energy, the biological sensor, processing device and transmitter are inactive and when the receiver is not receiving electromagnetic energy, the biological sensor, processing device and transmitter are inactive.

4 Claims, 9 Drawing Sheets

US 9,936,876 B2

ROBUST POWERING OF IMPLANTABLE BIOSENSOR PLATFORM

RELATED APPLICATIONS

This application claims priority to and benefit of the filing date of U.S. Provisional Patent Application Ser. No. 61/452, 912, filed Mar. 15, 2011, the contents of which are incorporated by reference herein in its entirety.

STATEMENT REGARDING FEDERALLY SPONSORED RESEARCH

The United States Government has certain rights in this invention pursuant to National Institute of Health [NIH-SBIR#1R43EB011886 Needle-Implantable, Wireless Multi-Sensor for Continuous Glucose Monitoring] and National Science Foundation [NSF-SBIR# IIP-1046902, Self-Calibrating, Wireless, Needle Implantable Sensor for Continuous Glucose Monitoring] Grants.

FIELD OF THE INVENTION

This invention relates generally to implantable bio sensors and more particularly to an improvement in implantable bio sensor platforms which allows for the robust powering of the implantable bio sensors.

BACKGROUND OF THE INVENTION

Implantable biomedical devices such as biosensors and pacemakers are powered by batteries contained in their hermetically sealed packages. While, some implanted devices are powered by electromagnetic induction and communicate with the external units via radio frequency (RF) wireless communication, some implanted units use energy harvesting devices that utilizes body motion to extract power and store it in a rechargeable device, such as a battery and/or a capacitor. In addition, solar cells, receiving radiation from an outside source, are used to power devices that are implanted in the body.

Unfortunately, many of these devices are prone to variations in the environment and/or conditions of the body. These various can affect the implanted device and its circuits which are prone to fluctuations that adversely affect the functionality of devices (including biosensors) that are used to monitor important analyte and other chemical concentrations within the body. For example, the power generated by the RF or solar powered units that power the device may not stable and thus may vary depending on the environmental changes or patient behavior. This is undesirable because the device may not function correctly and/or the data received/measured/transmitted may be incorrect and/or corrupted.

SUMMARY OF THE INVENTION

A method for measuring a biological characteristic of a body using an implantable biosensor device which is located in the body and which is powered by a solar cell/storage capacitor combination is provided, wherein the method includes transmitting light from a light source to the implanted biosensor device such that the transmitted light is received by the solar cell, wherein the light source is located external to the body and wherein the implanted biosensor device includes, an internal photodetector receiver, an optical transmitter, a biosensing device, a signal processing unit, and mode select logic circuits that are powered by the storage capacitor and that are configured to sense and calibrate the biological characteristic, and wherein the output of the solar cell is connected to the storage capacitor via a transistor switch which is turned on when the light is received by the solar cell and turned off when the light is not received by the solar cell, wherein the mode select logic circuits have outputs which are selectable via a finite state machine architecture and which are activated via an internal photodetector, wherein the internal photodetector is configured to receive a light wavelength that is different from an external unit and which is configured to generate pulses that can be used to enable selected outputs of the mode select logic unit, operating the bio sensor device to obtain biological characteristic data by sensing the biological characteristic; and transmitting optically the biological characteristic data to an external photodetector receiver.

An implantable device for measuring biological information of a body is provided and includes a plurality of solar cells, connected in series and parallel and configured to receive optical energy and convert the optical energy into electrical energy; a storage capacitor associated with the plurality of solar cells such that the electrical energy is received by and stored in the storage capacitor; a biological sensor; a sensor potentiostat interface; a signal processing device; a multiplexer unit; an optical transmitter; and an electronic driver, wherein the biological sensor and its potentiostat interface, signal processing device and optical transmitter are configured to receive the electrical energy from the storage capacitor, and wherein the biological sensor and signal processing device are configured such that during a first interval of time when the plurality of solar cells are receiving optical energy, the biological sensor and signal processing device are active and transmitting the biological information via the optical transmitter, and when the plurality of solar cells are not receiving optical energy, the biological sensor, signal processing device and transmitter are active for a different second interval of time, the duration of the second interval of time being determined by a discharging time constant of the storage capacitor, wherein the biological information is relatively free from interference from the optical source that powers the solar cells.

An implantable device for measuring biological information of a body is provided and includes solar cells configured to receive optical energy and convert the optical energy into electrical energy; a rechargeable battery associated with the solar cells via a transistor switch, wherein when the transistor switch is enabled, the solar cells and rechargeable battery are connected such that the electrical energy flows between the solar cells and the rechargeable battery, and when the transistor switch is disabled, the solar cells and rechargeable battery are not connected such that no electrical energy flow between the solar cells and the rechargeable battery; at least one biological sensor; a signal processing device; and mode select circuitry which is configured to operate as a finite-state machine and which is communicated with an external transmitter and an internal photodetector receiver and which is configured to enable the selection of the at least one biological sensor via a mode select unit responsive to electrical energy received from the solar cells; and wherein the biological sensor, its potentiostat interface, signal processing device and optical transmitter are configured to receive electrical energy from the rechargeable battery, and wherein the at least one biological sensor, signal processing device and optical transmitter are configured such that when the solar cells are receiving optical energy, the at least one biological sensor, signal processing device and optical transmitter are active and when the solar cells are not receiving optical energy, the at least one biological sensor, its potentiostat interface, signal processing device and optical transmitter are active for a predetermined limited time duration to prevent energy drain from the rechargeable battery.

An implantable device for measuring biological information of a body is provided, wherein the implantable device includes a receiver for receiving electromagnetic energy and converting the electromagnetic energy into electrical energy; a storage capacitor associated with the receiver such that the electrical energy from the receiver is stored in the storage capacitor; a biological sensor; a processing device; and a transmitter, wherein the biological sensor, processing device and transmitter are configured to receive electrical energy from the storage capacitor, and wherein the biological sensor, processing device and transmitter are configured such that when the receiver is receiving electromagnetic energy, the biological sensor, processing device and transmitter are inactive and when the receiver is not receiving electromagnetic energy, the biological sensor, processing device and transmitter are inactive.

A method for measuring a biological characteristic of a body using an implantable biosensor device which is located in the body and which is powered by a solar cell/storage capacitor combination is provided, wherein the method includes transmitting light from a light source to the biosensor device such that the transmitted light is received by the solar cell, wherein the light source is located external to the body and wherein the bio sensor device includes a receiver, a transmitter, a sensing device, a processing device and logic circuits that are powered by the storage capacity and that are configured to sense the biological characteristic, and wherein the output of the solar cell is connected to the storage capacitor via an interconnect switch which is turned on when the light is received by the solar cell and turned off when the light is not received by the solar cell; operating the biosensor device to obtain biological characteristic data by sensing the biological characteristic; and transmitting the biological characteristic data to an external receiver.

An implantable device for measuring biological information of a body is provided, wherein the implantable device includes a receiver for receiving electromagnetic energy and converting the electromagnetic energy into electrical energy; a rechargeable battery associated with the receiver via an interconnect switch, wherein when the interconnect switch is enabled the receiver and rechargeable battery are connected such that the electrical energy flows between the receiver and the rechargeable battery, and when the interconnect switch is disabled the receiver and rechargeable battery are not connected such that no electrical energy flow between the receiver and the rechargeable battery; a plurality of biological sensors a processing device; a finite-state machine, communicated with the receiver and configured to enable the selection of the plurality of bio sensors responsive to electrical energy received from the receiver; and a transmitter, wherein the biological sensor, processing device and transmitter are configured to receive electrical energy from the rechargeable battery, and wherein the plurality of biological sensors, processing device and transmitter are configured such that when the receiver is receiving electromagnetic energy, the biological sensor, processing device and transmitter are inactive and when the receiver is not receiving electromagnetic energy, the biological sensor, processing device and transmitter are inactive.

BRIEF DESCRIPTION OF THE FIGURES

The foregoing and other features and advantages of the present invention will be better understood from the following detailed description of illustrative embodiments, taken in conjunction with the accompanying drawings in which.

DETAILED DESCRIPTION OF THE INVENTION

This disclosure describes the present invention which includes robust remote powering and operation of a miniaturized micro-optoelectronic chip platform implanted in a body under the skin (human and/or animal). The platform may include a number (one or more) of devices including multiple biosensors, potentiostats and other circuit interfacing sensors, signal processing electronics, and wireless communication devices. The power may be remotely transmitted from an external unit transmitting light which is received by a series of solar cells that charge a capacitor and/or a rechargeable battery large enough to hold a charge during the time light is not transmitted, received or that undergoes fluctuations due to any number of factors. In one embodiment, it is shown that charging and discharging of the capacitor, when the light powering source is pulsed, can be used to generate a clock signal to internal control logic circuits which create a code that enables execution of various functions such as sensor selection and calibration and checking status of other devices critical to the functioning of the entire system.

Figure 1:
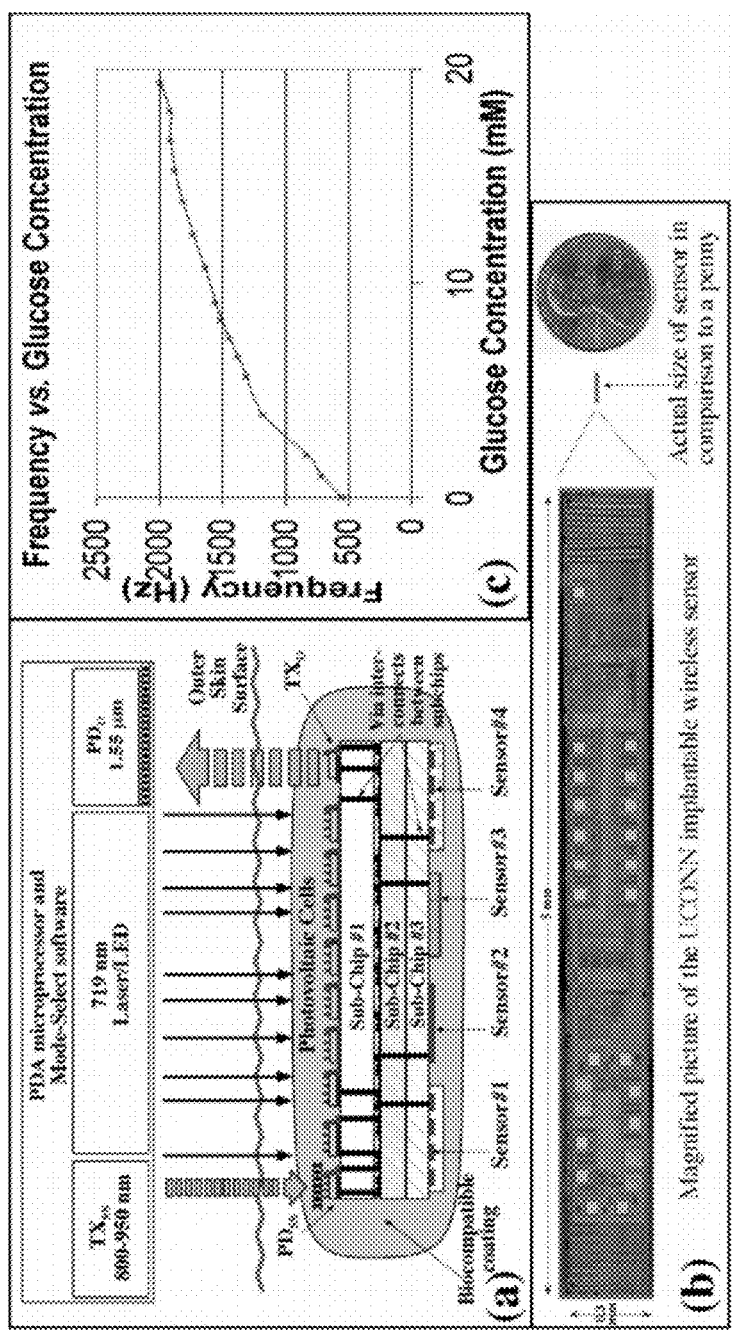
FIG. 1 illustrates an implantable platform having solar cells as a powering source packaged in one unit along with signal processor and optical devices for wireless communication, in accordance with the prior art.

Referring to FIG. 1, a schematic block diagram of a miniaturized solar powered implantable platform of an analyte sensor platform is shown in accordance with the prior art. Miniaturized photovoltaic cells are used to power the implanted unit (sub-chip #1). The sensor responses from sub-chip #3 are processed by the analog-to-digital converter (ADC) unit, converting sensor current into digital pulses that are then transmitted through the skin as optical pulses by the 1.5 μm $TX_D$ transmitter. An additional transmitter ($TX_{SS}$) and receiver ($PD_{SS}$) combination is used to optically transmit commands from the PDA unit to the implanted sensor platform and sequentially interrogate different sensors, potentiostat settings, calibration, and initialization routines. All three sub-chips are encapsulated within a composite hydrogel coating, containing a variety of tissue response modifiers (TRMs) to control tissue response and induce neoangiogenesis.

Figure 2:
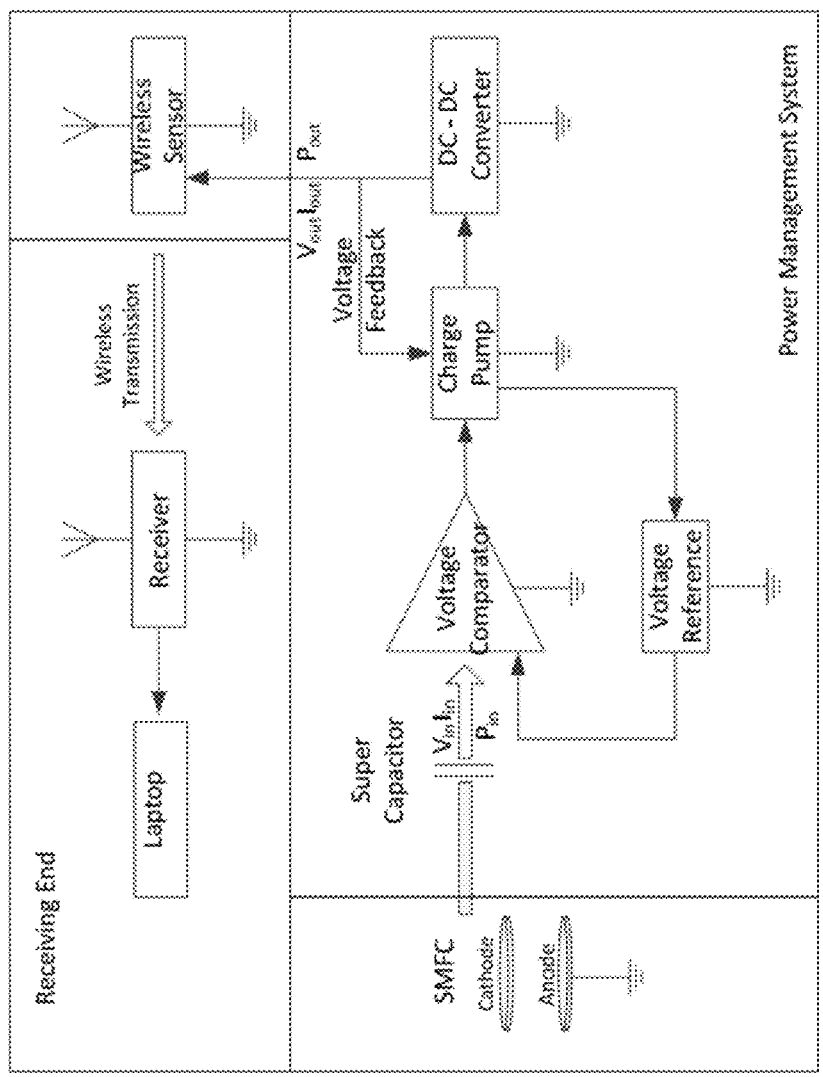
FIG. 2 illustrates a schematic block diagram of a power management device of a wireless sensor powered by sediment microbial fuel cell (SMFC) as the power source and using a storage capacitor, in accordance with the prior art.

Referring to FIG. 2, a schematic block diagram of a battery-less wireless sensor powered by sediment microbial fuel cell (SMFC) in accordance with the prior art is shown, where the SMFC powering unit using a storage capacitor. In addition, there is a telemetry system and a power management system [PMS] which converts the SMFC energy to power the sensors. It also decides when to operate and to stop depending on the output of the fuel cell. A wireless sensor measures the desired data and transmits using electromagnetic telemetry. The size of the storage super capacitor is determined by the dissipation in the sensor electronics.

Figure 3:
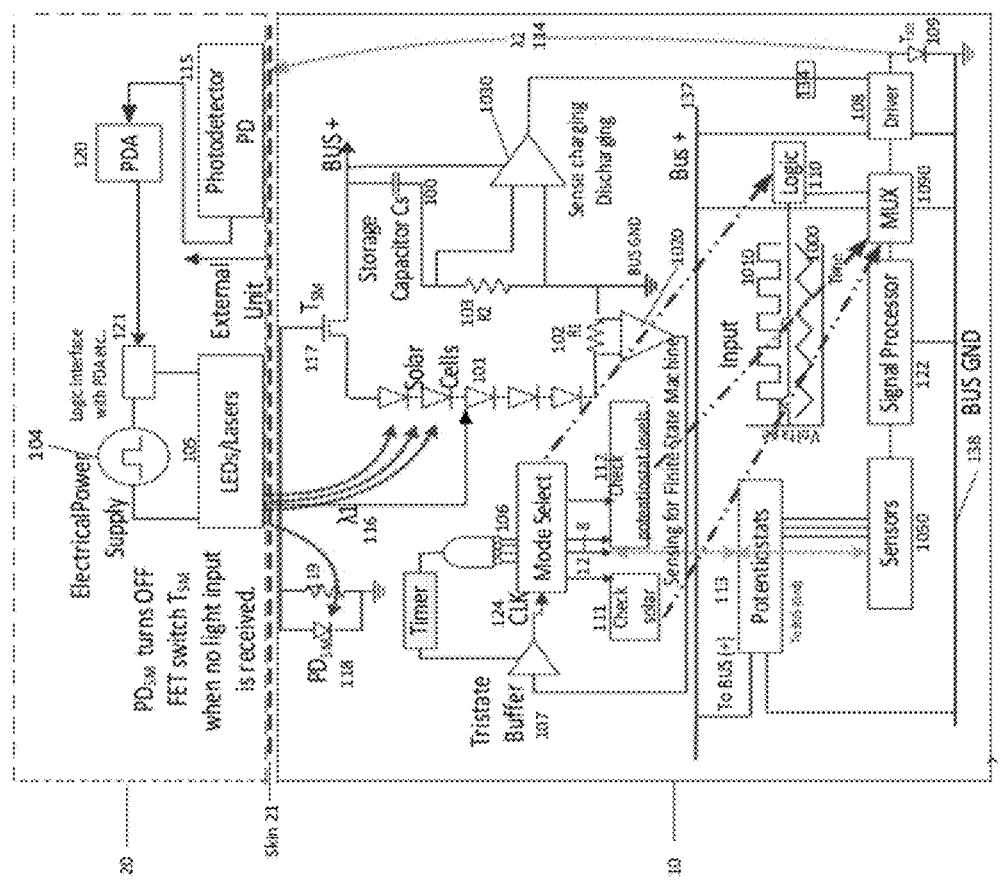
FIG. 3 illustrates a schematic block diagram of a pulsed light source powered solar cells configured to deliver power to an implantable platform having a storage capacitor as a robust power source, in accordance with an embodiment of the present invention.

Referring to FIG. 3, a schematic block diagram of pulsed light source powered solar cells configured to deliver power to an implantable platform having a storage capacitor as a robust power source mitigating fluctuations in power delivered to various electronic circuits and optical communication devices is shown in accordance with one embodiment of the present invention. It should be appreciated that the circuit of FIG. 3 may be configured to generate an internal clock signal that may be used to run the timing of a finite-state machine architecture enabling various functions such as (but not limited to) sensor selection and calibration, potentiostat check, sensor reading, and checking the level of solar power. As can be seen, in this embodiment a storage capacitor 100 ($C_s$), located in the implantable unit 10, is charged by an array of solar cells 101.

The capacitor 100 is located in series with two resistors 102 (R1) and 103 (R2). A pulsed electronic source 104 is used to power the light source 105 (such as light emitting diodes and/or lasers and/or any other light source suitable to the desired end purpose) which in turn is used to power the solar cells 101 that deliver electrical power to the implantable platform 10 having the storage capacitor 100. It should be appreciated that in this embodiment the storage capacitor 100 is used as a robust power source which mitigates the fluctuations in the power delivered to various electronic circuits and optical communication devices associated with the implantable platform 10. It should be appreciated that the circuit of FIG. 3 may be configured to generate an internal clock signal that may be used to run the timing of a finite-state machine architecture enabling various functions such as (but not limited to) sensor selection and calibration, potentiostat check, sensor reading, and checking the level of solar power.

Figure 4:
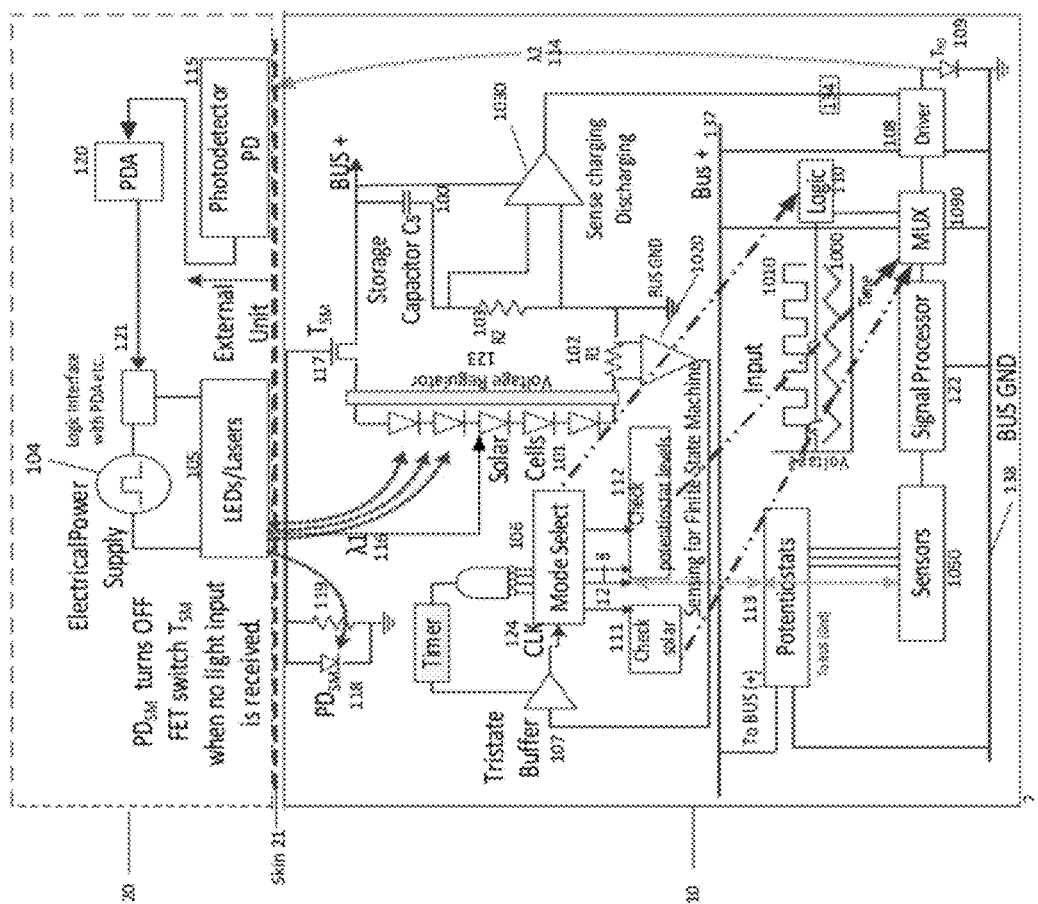
FIG. 4 illustrates a schematic block diagram showing a solar powered unit having a voltage regulator and storage capacitor, in accordance with an embodiment of the present invention.

It should be appreciated that one embodiment of a light-powered solar cell based powering device using a storage capacitor 100 interface, in accordance with the present invention, may operate as described hereinafter. A light source 105 (such as a light emitting diode, a laser diode or other light source) in an external unit 20 (which may be powered by an electrical power supply 104) located outside the skin 21 of a body in which the platform is implanted, provides light energy (such as light pulses) to power the solar cells 101 (which may be connected in series and/or parallel) to provide the voltage and current levels required by the circuits and devices they power which are associated with (such as being located on) the implantable platform unit 10. The duration for which the light is ON and OFF may be determined by the characteristics of the bio sensors or sensors 1050 and associated devices that are used to measure data and that provide the information (such as glucose or other analyte levels) desired by the operator. If more voltage stability is needed, the solar output may be fed to a voltage regulator 123 (as shown in FIG. 4) that produces a constant voltage in case the received light is fluctuating. The voltage regulator 123 interfaces with the energy storage capacitor $C_s$ 100 which is selected to be large enough to provide electrical power to circuits and devices that need electrical power for their operation (such as via an electrical bus distribution 137 and 138).

As shown in FIG. 3, the capacitor $C_s$ 100 charges when the light pulses are ON and discharges when the light pulses are OFF (i.e. received light by the solar cells is OFF). Two small resistors (R1 102 and R2 103) may be used to generate voltage pulses using circuits 1020 and 1030, respectively. One of the resistors R1 102 may be used to generate a clock signal CLK 124 that controls the output of a MODE SELECT logic block 106. That is, depending on the number of pulses, the Mode Select logic block 106 enables one of eight outputs (or higher number of outputs) as High and the rest of them are Low. The clock 124 may be derived by enabling a tri-state buffer type circuit 107. The other resistor R2 103 may be used to enable the driver 108 via a logic block 134 that interfaces with the transmitter $T_{XD}$ 109. The driver 108 receives a signal from one of the sensors represented as 1050 via MUX 1090 that is controlled by a Logic block 110 which enables the MUX 1090, where the MUX input comes from various check circuit blocks 111 and 112 when they are enabled by the Mode Select 106. The finite-state machine code-enabled output of the Mode Select 106 in turn enables the desired Sensor 1050 and its potentiostat 113, and the sensor output may be processed by the Signal Processor 122. The sensor signal, permitted by the MUX 1090 and associated Logic Block 110, is fed to the Driver 108 and $T_{XD}$ 109. The light output 114 (shown by wavelength λ2) is transmitted to the photodetector PD 115 located in the external unit 20. The photodetector 115 is interfaced with a display device such as PDA 120 (or, cell phone, or laptop device or other suitable device). This PDA or cell phone or laptop device 120 may also be used to control the electrical supply 104 which powers the optical powering source 105. The electrical power supply 104 is in turn interfaced with a logic block or a microcontroller 121.

Also in accordance with the present invention, the finite-state machine works in such a way that the sensor output may be transmitted, powered by the storage capacitor 100, during the time when the light pulses are in the OFF state. That is, the solar cells 101 are not powered by the external powering source 105. Thus, the sensor data is transmitted by $T_{XD}$ 109 during the OFF cycle of the powering source 105. The waveforms, in the inset, show the square input pulses 1010. The output 1000 of $C_s$ 100 increases during charging and decreases in voltage magnitude during the OFF state or discharge cycle. This way the interference between the solar powering and optical communication link is avoided. In addition, the operating wavelengths of the powering source λ1 116 and that of output transmitter 109 $T_{XD}$ λ2 114 are different. The photodetector 115 has coatings that absorb any stray light λ1 116. Similarly, $T_{XD}$ 109 has coatings or filters that make it operation with minimal influence of light λ1 116. It should be appreciated that the use of different wavelengths (λ) reduces undesired interference of optical photodetectors, which generally have a broad spectral range. Thus, powering the devices using a first wavelength (λ1) and transmitting the data using a second wavelength (λ2) reduces the chance of interference because the λ1 photodetector 118 in the implantable unit 10 is not sensitive to wavelength λ2.

Moreover, the solar powering circuit may be configured to ensure that the solar cells are disconnected from the storage capacitor $C_s$ 100 during the OFF cycle (that is when no input powering light pulses are received from the external powering source 105). In one embodiment, a FET switch $T_{SM}$ 117 is used which in turn is enabled by the photodetector $PD_{SM}$ 118 which monitors the light received from the powering source 105. It should be appreciated that the photodetector $PD_{SM}$ 118 may have an interface that uses a trans-impedance amplifier rather than a simple resistor 119 as shown. Additionally, the output of analog bio sensors' 1050 may be processed by a signal processor 122 and in turn fed to the MUX 1090.

Referring to FIG. 4, a schematic block diagram of a solar powered unit having a voltage regulator 123 whose output is fed to the storage capacitor 100 in accordance with an embodiment of the present invention is shown. This embodiment is similar to that of FIG. 3 in all other aspects. It should be appreciated that the voltage regulator may be a low drop output (LDO) regulator or other regulator as desired.

Figure 5:
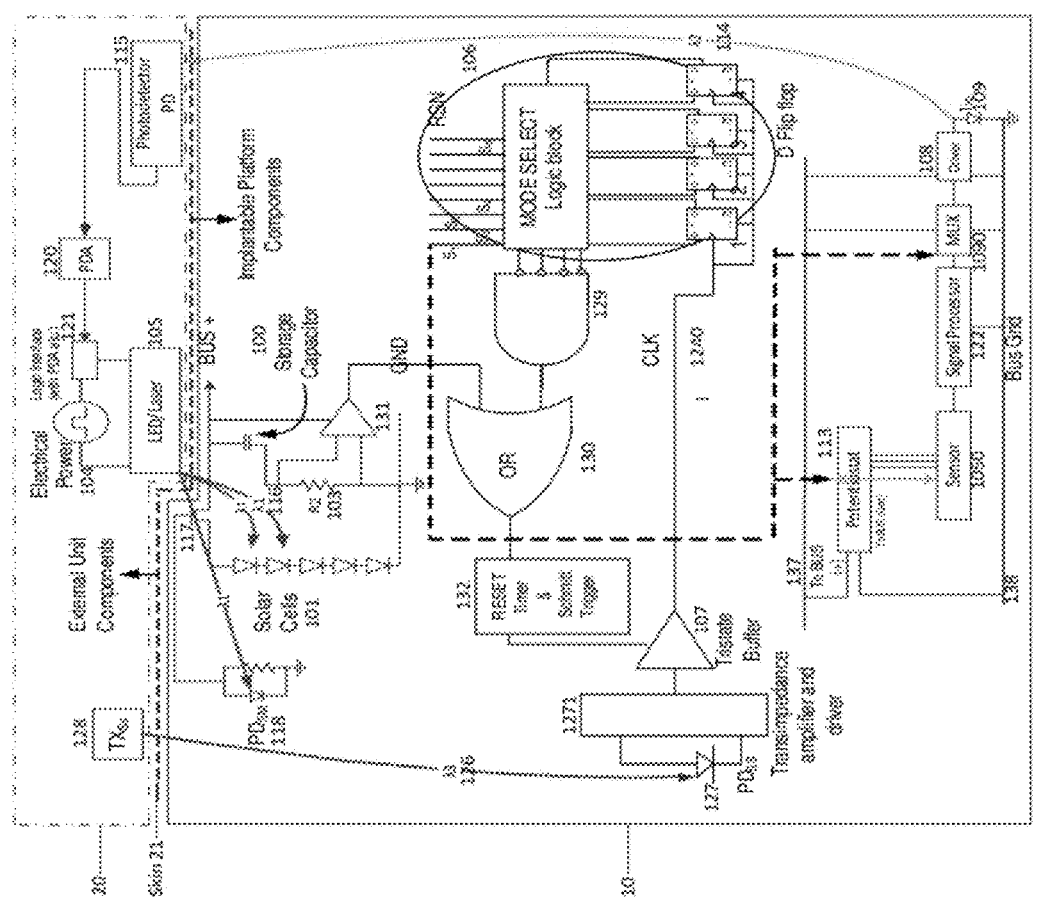
FIG. 5 illustrates a schematic block diagram of pulsed light source powered solar cells configured to deliver power to an implantable platform having storage capacitor for reducing fluctuations in the electrical output, in accordance with an embodiment of the present invention.

Referring to FIG. 5, a schematic block diagram of pulsed light source powered solar cells configured to deliver power to an implantable platform having a storage capacitor for reducing fluctuations in the electrical output is shown in accordance with another embodiment of the present invention. It should be appreciated that the solar cell interface here is similar to that illustrated in FIG. 3. In this embodiment, the operation of the finite-state machine based clock generation method is different. The CLK 1240 that determines the operation of the Mode Select block 106 may be generated by another light signal λ3 126 which is received by a photodetector $PD_{SS}$ 127 located on the implanted platform 10. The light pulses at wavelength λ3 126 are transmitted by $TX_{SS}$ 128 located in the external unit 20 where the solar powering source 105 is also housed. The electrical output of 127 is shaped by a trans-impedance amplifier circuit 1271, which generates shaped electrical pulses of desire magnitude, and is fed to the tri-state buffer 107, which is enabled by a signal coming from a timer block 132. The timer 132 gets the input from the OR logic gate 130, which in turn gets two inputs (one from the Mode Select 106 unit's logic block 129 and the second from the resistor 103). The voltage signal from resistor 103 is shaped by unit processor 131. It should be appreciated that voltage signal from resistor 103 is shaped because the voltage signal produced by the resistor 103 is very small (may be in millivolts) and it is time varying because of charging and discharging of capacitor 100 (due to optical pulses powering the solar cells 101 even when a voltage regulator 123 is there). Accordingly, a wave shape and magnitude of this signal is used to perform the logic operations, wherein the wave shape and magnitude is responsive/dependent (at least in part) to the logic circuit configuration used.

In this embodiment, the tri-state buffer circuit 107 generates CLK 1240 pulses so long as the capacitor $C_s$ 100 has adequate charge and a corresponding voltage level value or Mode Select output via logic gate 129 is of appropriate value. However, in accordance with the present invention, it should be appreciated that the embodiment of FIG. 5 can be modified in a way that we do not need $PD_{SS}$ 127 to generate the CLK 1240. $PD_{SM}$ can be configured to serve two purposes: 1) the solar power level check and 2) the generation of CLK 1240 using the transimpedance amplifier 1271 and other circuits. In this case, $TX_{SS}$ 128 transmitter is not needed.

It should be appreciated that this circuit may also be configured to ensure that the solar cells are disconnected from the storage capacitor $C_s$ 100 during the OFF cycle (that is during the time when the input powering light pulses 116 incident on the solar cells 101 are not received from the external powering source 105). Similar to the embodiments shown in FIG. 3 and FIG. 4, this embodiment uses a FET switch $T_{SM}$ 117 which in turn is enabled by the photodetector $PD_{SM}$ 118. This helps to ensure that the capacitor 100 is not discharged by the solar cells.

Figure 6:
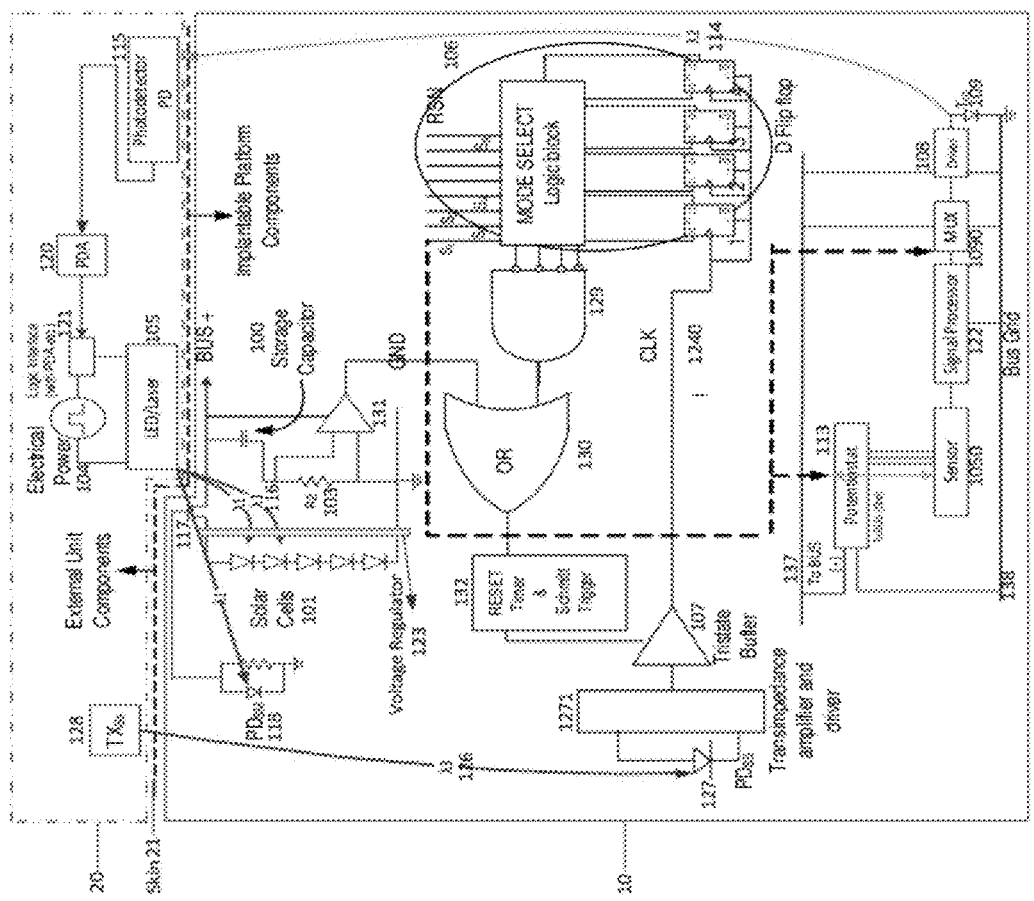
FIG. 6 illustrates a schematic block diagram of voltage regulated solar cells and storage capacitor combination powering implantable wireless biosensor platform with multi-sensor and multifunctional capability, in accordance with an embodiment of the present invention.

Referring to FIG. 6, a schematic block diagram illustrating a voltage regulator 123 being used in between the solar cells 101 and storage capacitor 100 is shown, in accordance with still yet another embodiment of the present invention. In this embodiment, the circuit has the functionality of not operating if the output is below a certain value. This is similar to the embodiment shown in FIG. 5 with the difference being that here a voltage regulator is used. Finite state machine pulsing is sent by the external transmitter like that shown in FIG. 5. This unit combines robust regulated solar powering of the implantable wireless bio sensor platform 10 with multi-sensor 1050 and multifunctional capability (via Mode Select logic block 106).

Figure 7:
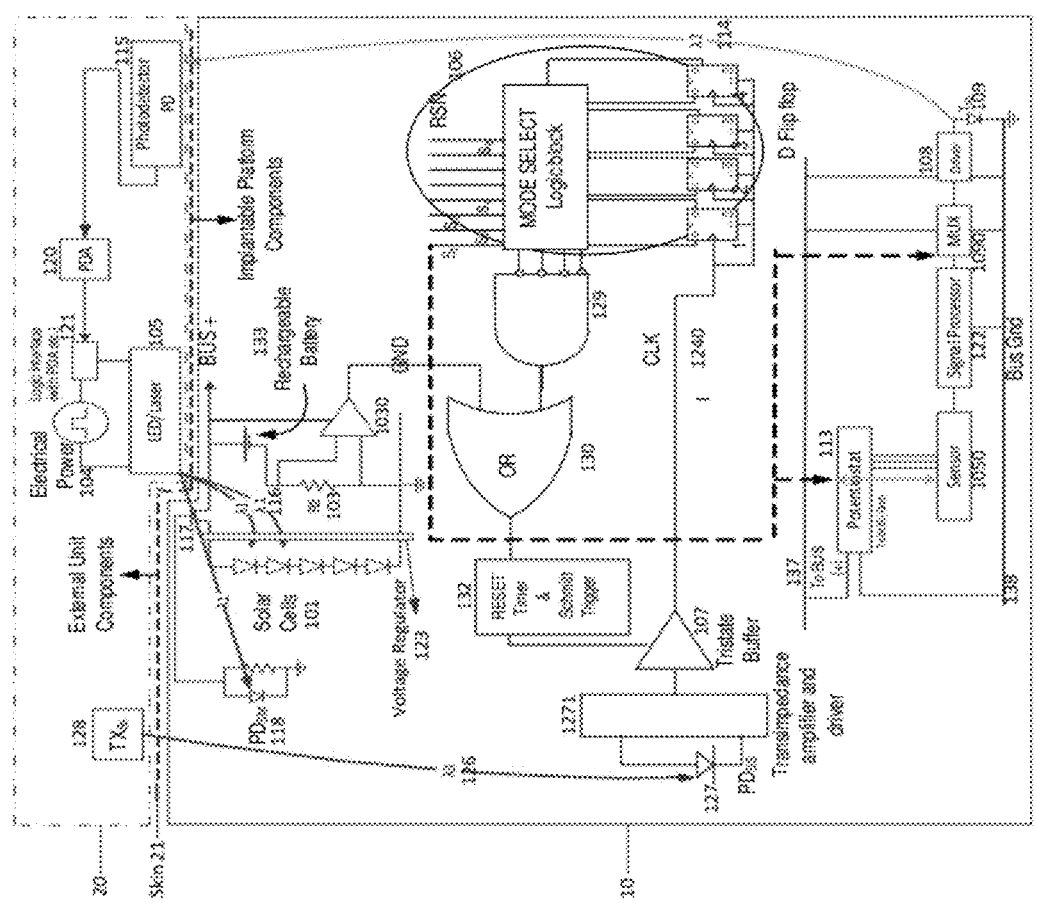
FIG. 7 illustrates a schematic block diagram of a solar cell and rechargeable battery powered implantable wireless bio sensor platform, in accordance with an embodiment of the present invention.

Referring to FIG. 7, a schematic block diagram illustrating a solar cell 101 and rechargeable battery 133 powered implantable wireless biosensor platform 10 is shown in accordance with still yet another embodiment of the invention. In this embodiment, the battery is charged during the ON time when solar cells 101 receive the powering light 116 pulses. When the light is OFF, the battery 133 provides the power.

Figure 8:
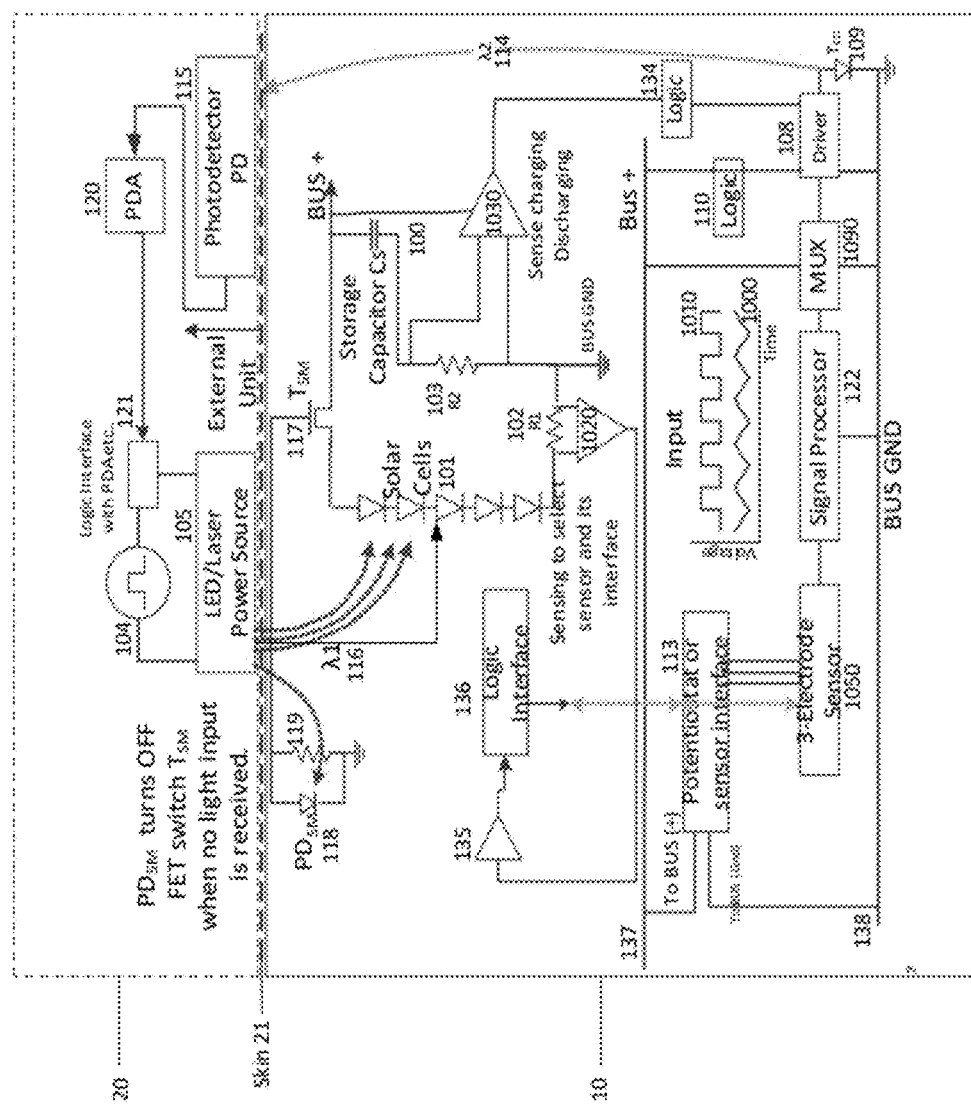
FIG. 8 illustrates a schematic block diagram of a solar-capacitor combination powered device configured to read analyte levels during the time a light pulse is ON and transmits it after a certain interval when it is turned OFF, in accordance with an embodiment of the present invention.

Referring to FIG. 8, a schematic block diagram illustrating a solar cell 101-storage capacitor 100 combination power device is shown in accordance with still yet another embodiment of the invention. In this embodiment, the solar cell 101-storage capacitor 100 combination is used to power the implantable unit 10 which measures analyte levels using three (3)-electrode sensors 1050 (interfacing with potentiostats 113) during the time interval when the powering light pulse (λ1) 116 is ON. The sensor data in terms of pulse frequency (for example, obtained by converting the sensor 1050 current signal by the signal processor 122 into pulses) is transmitted via the transmitter 109 during the time when powering light 116 pulses are turned OFF. The beginning of the OFF state (or ending of the ON state of the light pulse) may be determined by sensing the voltage (which may be small) developed across two resistors R1 102 and R2 103. The electrical signal across R2 103 is processed by 1030 which enables logic block 134 (for example, using the falling edge voltage detection circuits), that in turn activates the driver 108 fed to the transmitter $TX_D$ 109. The voltage pulses across resistor R1 102 are used to enable the logic 135 and logic interface 136, which in turn selects a sensor and its associated circuits (potentiostat 113) and connects them to the BUS lines 137 and 138 supplying power. The solar power check is accomplished by photodetector 118. Similar to the embodiments shown in FIG. 3 and FIG. 4, the circuit of this embodiment uses a FET switch $T_{SM}$ 117 which in turn is enabled by the photodetector $PD_{SM}$ 118. This ensures that the capacitor 100 is not discharged by the solar cells.

It should be appreciated that as discussed above, the present invention advantageously allows for the power output of solar cells to be stabilized to account for any fluctuations in ambient and other operating conditions. Moreover, the present invention permits optical data transmission (analyte level/sensor output or other info) by transmitter 109 during the OFF time (that is when solar cells 101 are not getting any power from 105). This advantageously minimizes interference of the photodetectors in the external unit. Additionally, the present invention provides for a clock (CLK) to be generated using an external device (such as transmitter 128 and photodetector 127 set (FIGS. 5, 6, 7)). This CLK advantageously permits (via the Mode Select logic block 106) functions to be enabled (such as sensor selection, calibration etc.) In one embodiment, the present invention uses the capacitor (which generates ripples 1000 (FIGS. 3, 4, 8) due to charging and discharging) to generate CLK 124 (see FIGS. 3 and 4) without using an external transmitter (such as $TX_{SS}$ 128 and photodetector 127). Furthermore, it is contemplated that the capacitor generated ripple signal can be used to auto calibrate biosensors as their performance degrades due to biofouling or negative tissue response. It should also be appreciated that the present invention may be used with any implantable device that is powered via an external source, regardless of the type of external powering source.

Figure 9:
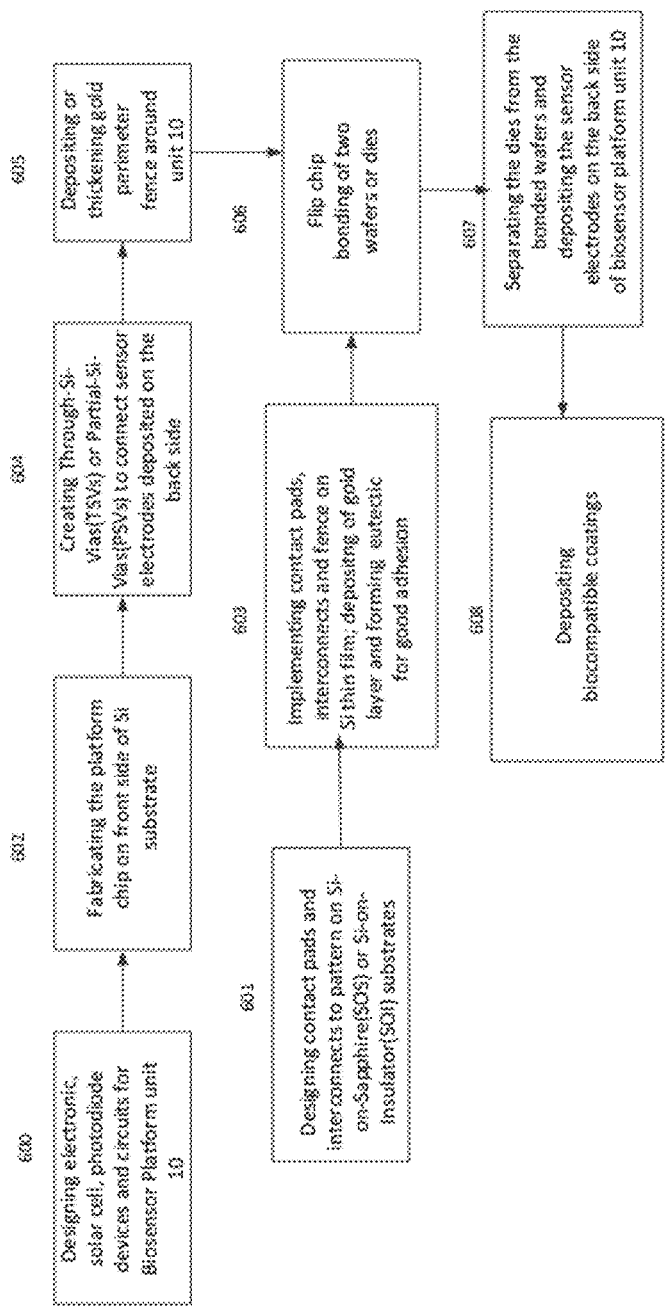
FIG. 9 illustrates an operational flow diagram of a method for creating an implantable platform, in accordance with an embodiment of the present invention.

Referring to FIG. 9, an operational flow diagram of a method 599 for creating an implantable platform, in accordance with one embodiment of the present invention is shown and may be conducted in any order suitable to the desired end purpose. This method includes designing the bio sensor platform of the present invention, as shown in operational block 600. This may be accomplished by configuring the layout of the primary and secondary circuits for the platform. The method further includes fabricating the platform chip on the front side of an Si substrate, as shown in operational block 602. It is contemplated that substrates other than Si may be used. At this point, the sensor electrode pads may be deposited on the back side of the Si substrate after creating through-Si-Vias (TSVs) or Partial-Si-Vias (PSVs), as shown in operational block 604. These may connect the sensor electrodes, as shown in operational block 607. A gold perimeter fence may be formed around the perimeter, as shown in operational block 605, where the fence may be deposited or thickened. Additionally, contact pads and interconnects to pattern Si film on Si-on-Sapphire (SOS) or Si-on-Insulator (SOI) substrates may be designed, as shown in operational block 601. Contact pads and interconnects and the gold fence may be implemented on an Si thin film and a gold layer may be deposited to form eutectic (for good adhesion), as shown in operational block 603. These two wafers 605, 603 (or matching dies from these wafers) may then be flip-chip bonded, as shown in operational block 606. The dies may be separated from the bonded wafers and the sensor electrodes may be deposited on the back side the biosensor platform, as shown in operational block 607. The biocompatible coatings may then be deposited onto the biosensor platform, as shown in operational block 608.

It should be further appreciated that the present invention allows for the powering of implantable biomedical devices using solar cells in conjunction with a storage capacitor. The storage capacitor advantageously enhances the robustness and makes the biasing independent of the fluctuations in the powering process of the solar cells. In one embodiment, the solar cells are powered by light pulses that are absorbed by the photovoltaic devices producing an electrical output. This output is fed to a voltage regulator that produces a constant voltage and takes care of fluctuations in the light pulse intensity due to a variety of reasons or conditions. The voltage regulator is connected to a capacitor that is charged by the solar cells' output during the time the light pulses are ON and stores the energy. The capacitor then discharges during the time the light pulses are OFF. However, the electronic circuits that interface with biosensors or other devices on the implanted platform are continuously getting power and operating as designed. The charging and discharging of the capacitor is also used to generate a clock that is used to trigger a finite-state machine which is used to control the logic in a Mode Select Unit enabling various control functions including sensor selection, sensor calibration, potentiostat check and various checking functions. In addition, the design is such that it transmits the desired data out wirelessly during a designated time interval (such as during the time light pulses are in OFF state).

In accordance with the present invention, the processing of the method of the invention as described herein may be implemented, wholly or partially, by a controller operating in response to a machine-readable computer program. In order to perform the prescribed functions and desired processing, as well as the computations therefore (e.g. execution control algorithm(s), the control processes prescribed herein, and the like), the controller may include, but not be limited to, a processor(s), computer(s), memory, storage, register(s), timing, interrupt(s), communication interface(s), and input/output signal interface(s), as well as combination comprising at least one of the foregoing.

Moreover, the method of the present invention may be embodied in the form of a computer or controller implemented processes. The method of the invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

It should be appreciated that while the invention has been described with reference to an exemplary embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. For example, it is considered within the scope of the invention, that various other components, circuit combinations and circuit elements may be used to accomplish the desired and contemplated functionality. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. An implantable device for measuring biological information of a body, the implantable device comprising:
a plurality of solar cells, wherein the plurality of solar cells include at least two arrays, and wherein the at least two arrays include cells connected in series and wherein the at least two arrays are connected in parallel and configured to receive optical energy from an optical source located in an external unit and convert the optical energy into electrical energy;
a storage capacitor associated with the plurality of solar cells such that the electrical energy is received by and stored in the storage capacitor;
a biological sensor;
a mode select configured to receive commands from an external unit;
a sensor potentiostat interface;
a signal processing device;
a multiplexer unit;
an optical transmitter; and
an electronic driver, wherein the mode select unit receives commands from the external unit in the form of optical energy, and wherein a first internal photodetector receiver is located on the implantable device and configured to receive the commands and convert the commands into electrical signals, and wherein the mode select is configured to operate as a finite state machine, and where in the mode select enables selection of at least one biological sensor, and wherein the electronic driver is configured to receive signals from the multiplexer unit, and wherein the multiplexer unit is configured to receive electrical signals from the signal processing device, and wherein the multiplexer unit is connected to a logic block and wherein logic block is enabled by the mode select unit, and wherein the biological sensor and its potentiostat interface, signal processing device and optical transmitter are configured to receive the electrical energy from the storage capacitor, and
wherein the biological sensor and signal processing device are configured such that during a first interval of time when the plurality of solar cells are receiving optical energy, the biological sensor and signal processing device are active and transmitting the biological information via the optical transmitter,
and when the plurality of solar cells are not receiving optical energy, the biological sensor, signal processing device and transmitter are active for a different second interval of time,
the duration of the second interval of time being determined by a discharging time constant of the storage capacitor, wherein the biological information is relatively free from interference from the optical source that powers the solar cells.

2. The implantable device of claim 1, where the mode select is further configured to receive code generated by at least one of,
the charging and discharging of the storage capacitor without the use of a first internal photodetector, and
an external transmitter located in the external unit and configured to send the code optically for the finite state machine, and wherein the first internal photodetector receiver is further configured to receive the code.

3. The implantable device of claim 1, wherein the optical source is located in the external unit and includes at least one of a light-emitting diode, a laser diode, a fluorescent lamp and an incandescent lamp.

4. An implantable device for measuring biological information of a body, the implantable device comprising:
a plurality of solar cells, wherein the plurality of solar cells include at least two arrays, and wherein the at least two arrays include cells connected in series and wherein the at least two arrays are connected in parallel and configured to receive optical energy from an optical source located in an external unit and convert the optical energy into electrical energy;
a storage capacitor associated with the plurality of solar cells to receive the electrical energy, such that the electrical energy is stored in the storage capacitor;
a photodetector circuit configured to receive optical energy from the optical source;
an electronic switch, wherein the electronic switch is connected to the plurality of solar cells and the photodetector circuit and activated by the photodetector circuit,
wherein when the optical energy received from the optical source is not sufficient, the electronic switch disconnects the storage capacitors from the plurality of solar cells,
a biological sensor;
a mode select configured to receive commands from an external unit;
a sensor potentiostat interface;
a signal processing device;
a multiplexer unit;
an optical transmitter; and
an electronic driver, wherein the mode select unit receives commands from the external unit in the form of optical energy, and wherein a first internal photodetector receiver is located on the implantable device and configured to receive the commands and convert the commands into electrical signals, and wherein the mode select is configured to operate as a finite state machine, and where in the mode select enables selection of at least one biological sensor, and wherein the electronic driver is configured to receive signals from the multiplexer unit, and wherein the multiplexer unit is configured to receive electrical signals from the signal processing device, and wherein the multiplexer unit is connected to a logic block and wherein logic block is enabled by the mode select unit, wherein the biological sensor and its potentiostat interface, signal processing device and optical transmitter are configured to receive the electrical energy from the storage capacitor, and
wherein the biological sensor and signal processing device are configured such that during a first interval of time when the plurality of solar cells are receiving optical energy, the biological sensor and signal processing device are active and transmitting the biological information via the optical transmitter,
and when the plurality of solar cells are not receiving optical energy, the biological sensor, signal processing device and transmitter are active for a different second interval of time,
the duration of the second interval of time being determined by a discharging time constant of the storage capacitor, wherein the biological information is relatively free from interference from the optical source that powers the solar cells,
wherein the storage capacitor is in series with circuits that generate voltage pulses that are used to generate clock signals that are used to control the output of the mode select, and wherein the circuits are used to enable the electronic driver.

\* \* \* \* \*